United States Patent [19]

Modrovich

[11] Patent Number: 4,965,210

[45] Date of Patent: Oct. 23, 1990

[54] STABLE REAGENT FOR DETERMINING BILIRUBIN IN SERUM AND METHOD OF PREPARATION

[76] Inventor: Ivan E. Modrovich, 96 Natalie Way, Camarillo, Calif. 93010

[21] Appl. No.: 357,023

[22] Filed: May 25, 1989

Related U.S. Application Data

[63] Continuation-in-part of Ser. No. 101,776, Sep. 29, 1987, abandoned.

[51] Int. Cl.[5] .................... G01N 21/78; G01N 33/72
[52] U.S. Cl. .................... 436/97; 436/166; 436/903
[58] Field of Search ................ 436/97, 166, 903

[56] References Cited

U.S. PATENT DOCUMENTS

| | | | |
|---|---|---|---|
| 3,585,004 | 6/1971 | Mast | 436/97 X |
| 3,989,462 | 11/1976 | Hirsch | 436/97 |
| 4,119,401 | 10/1978 | Sansur et al. | 436/97 |
| 4,311,483 | 1/1982 | Perry | 436/97 X |
| 4,612,290 | 9/1986 | Yazawa et al. | 422/56 X |

FOREIGN PATENT DOCUMENTS

| | | | |
|---|---|---|---|
| 0140642 | 8/1983 | Japan | 436/97 |
| 2039773 | 2/1987 | Japan | 436/97 |

OTHER PUBLICATIONS

Henry et al, "Clinical Chemistry-Principles and Technics", Second Edition, Harper & Row, New York, 1974, pp. 1045-1050.

*Primary Examiner*—Robert J. Hill, Jr.
*Attorney, Agent, or Firm*—Christie, Parker & Hale

[57] ABSTRACT

There is provided a bilirubin assay composition and method of its formation. The composition comprises water, EDTA, of water soluble organic sulfate present in a concentration of about 1 g/l to solution saturation, caffeine in a concentration of from 0 to about 100 g/l and a diazonium salt in a concentration of about 0.05 to about 1.5 mM. The solution has a pH of from about 3.5 to about 6.0 and is stable for at least 18 months at 2° to 8° C.

21 Claims, No Drawings

STABLE REAGENT FOR DETERMINING BILIRUBIN IN SERUM AND METHOD OF PREPARATION

This application is a continuation-in-part of Ser. No. 101,776, filed Sept. 29, 1987, now abandoned.

BACKGROUND OF THE INVENTION

Bilirubin is a reddish yellow substance found in biological substances such as blood serum, and has the empirical formula: $C_{33}H_{36}N_4O_6$ Its presence in serum at too high a level indicates jaundice and its measurement is used as a liver function test.

One standard assay used for the quantitive determination of bilirubin is the Jendrassik-Grof method which uses as the assay composition an aqueous solution of caffeine, a benzoate salt, an acetate salt and diazonium salt of sulfanilic acid formed by reacting sulfanilic acid and sodium nitrite in diluted hydrochloric acid. Bilirubin present in the serum reacts with the diazotized sulfanilic acid to form a chromophore in which the caffeine and benzoate and acetate salts cooperate to serve as an activator and speed the reaction.

The problem with the solution used is its stability. It is initially supplied as a three component system. One contains caffeine, the benzoate salt and the acetate salt. The second contains sulfanilic acid and hydrochloric acid. The third reagent contains sodium nitrite and is the least stable of the three. When the three components are combined, stability is less than 8 hours.

It would be desirable, therefore, to have a stable single reagent system which enables the measurement of bilirubin. Such a system would be lower in cost as three different components need not be packaged. It would also reduce the chance of human error which can occur in combining three components to make an assay reagent. This is because better quality control exist when all components can be added to form a single reagent in quite precise amounts. Such a reagent of adequate shelf life has not heretofore been proposed in the art in ready to use liquid form.

SUMMARY OF THE INVENTION

The present invention provides a single reagent system of an excellent shelf stability of at least 18 months at 2 to 8° C. and is highly responsive to the quantitative measurement of bilirubin concentration in biological fluids such as blood serum at 540 nanometers (nm).

The composition comprises an aqueous solution of at least about 1 gm/1 up to solution saturation of a water soluble organic sulfate which may be a long chain aliphatic sulfate, an aromatic sulfate or mixtures thereof; from about 0.05 to about 15 millimole per liter (mM) of a diazonium salt, preferably 3,5-dichlorophenol diazonium tetrafluoro-borate at a concentration of about 0.15 mM; from 0 to 100 g/1 preferably from about 2 to about 100 g/1 caffeine, and having metal complexing agent preferably ethylene-diaminetetracetic acid (EDTA) present in an amount sufficient to complex with heavy metal ions. Normally, EDTA concentration is about 2 g/1. Solution pH is from about 1.0 to about 6, preferably about 3.5 to about 5.5, and most preferably about 4.4.

The composition is prepared by first adding the complexing agent (EDTA) to water followed by dissolving the organic sulfate then dissolving the caffeine and finally dissolving the diazonium salt.

The resulting mixture is stable for at least 18 months at 2 to 8° C. which is a time sufficient to enable manufacture, worldwide shipment, warehousing and storage until use.

DETAILED DESCRIPTION

There is provided in accordance with the present invention a single reagent composition of excellent shelf life which enables the quantitive assay of bilirubin concentration in blood serum. The composition is an aqueous solution of at least one diazonium salt, preferably 3,5 dichlorophenol diazonium tetrafluoroborate, present in a concentration from about 0.05 to about 15 millimoles per liter (mM), more preferably, about 0.05 to about 1.5 mM, more preferably about 0.15 mM; 1 g/1 to solution saturation of a water soluble alkali salt of an organic sulfate where the organic moiety is a long chain aliphatic group, an aromatic group and mixtures thereof. The lithium salts are presently preferred and preferred organic sulfate is the lithium salt of dodecyl sulfate present in a preferred concentration of about 10 g/1. There is also present 0 to about 100 g/1 preferably from about 2 to about 100 g/1, more preferably about 10 g/1 caffeine and ethylenediaminetetraacetic acid (EDTA) in sodium salt form present in a concentration sufficient to complex with any heavy metal ion which are present. The current preferred concentration of EDTA is about 2 g/1.

The solution has a pH from about 1 to about 6, preferably about 4 to about 5, and most preferably about 4.4.

The composition is prepared by first adding EDTA to distilled water to complex any heavy metals which are present, the water soluble organic sulfates are added and dissolved, followed by addition of and dissolving of caffeine. The diazonium salt is added last. The solution as prepared is stable at temperatures of about 2 to about 8° C. (refrigeration conditions) for at least 18 months.

In the system, the diazonium salt diazotizes with bilirubin forming a chromogen which is red in color. The water soluble organic sulfate acts to catalyze the diazo reaction, make the complex absorbance more intense and stabilizes the diazonium salt against degradation. Caffeine accelerates the formation of the complex and intensifies the color to make the absorbance higher.

In use, approximately one milliliter of the preferred composition and about 50 microliters of the serum are combined. Any bilirubin present is diazotized to form a red chromogen whose intensity is measured at 540 nanometers to eliminate interference attributed to hemaglobin, lipemia and the like which obscure the presence of bilirubin if absorbance is measured at 515 nanometers where maximum absorbance occurs. Making the determination at 540 nanometers, the interference is minimized and the bilirubin present reacts to provide the intense color enabling measurement.

The assay system of this invention is suited to the measurement of total bilirubin including unconjugated and/or conjugated fractions.

What is claimed is:

1. A liquid assay composition for determining total bilirubin in biological fluids which comprises an aqueous solution of water, a complexing agent present in a concentration sufficient to complex heavy metals, from about 0.05 to about 15 mM of at least one diazonium salt, from about 1 g/1 to solution saturation of a water soluble organic sulfate, and from 0 to about 100 g/l caffeine, and wherein said composition has a pH from about 1.0 to about 6.0 and is stable at least 18 months at 2° C. to 8° C.

2. A composition is claimed in claim 1 in which caffeine is present in an amount of from about 2 to about 100 g/l.

3. A composition as claimed in claim 1 in which the at least one diazonium salt is 3,5 chlorophenol diazonium tetrafluoroborate.

4. A composition as claimed in claim 3 in which the water soluble organic sulfate is an alkali metal salt of dodecyl sulfate.

5. A composition as claimed in claim 4 in which the diazonium salt concentration of the composition is about 0.15 mM.

6. A composition as claimed in claim 1 in which the water soluble organic sulfate is selected from the group consisting of long chain aliphatic sulfates, aromatic sulfates and mixtures thereof.

7. A composition as claimed in claim 1 in which the water soluble organic sulfate is an alkali metal salt of dodecyl sulfate.

8. A composition as claimed in claim 1 in which the diazonium salt concentration of the composition is about 0.15 mM.

9. A composition as claimed in claim 8 which composition has a pH of about 3.5 to 5.5.

10. A composition as claimed in claim 9 in which the complexing agent is ethylenediaminetetraacetic acid present in a concentration of about 2 g/l.

11. A composition as claimed in claim 1 which composition has a pH is from about 3.5 to about 5.5.

12. A composition as claimed in claim 1 in which the complexing agent is ethylenediaminetetraacetic acid present in a concentration of about 2 g/l.

13. A liquid assay composition for the quantitative determination of bilirubin which comprises an aqueous solution containing about 2 g/l ethylenediaminetetraacetic acid, about 0.15 mM of 3,5 dichlorophenol diazonium tetrafluoroborate, about 10 g/l of a lithium salt of dodecyl sulfate, and wherein said composition has a pH of about 4.4 and is stable at 2° C. to 8° C. for at least 18 months.

14. A method for forming a stable liquid assay composition suitable for determining total bilirubin in biological fluids at 540 nanometers which comprises forming a solution by dissolving at least one complexing agent in water in an amount sufficient to complex heavy metal ions, followed by dissolving in the solution of water and complexing agent at least one water soluble organic sulfate to a concentration of from about 1 g/l to solution saturation, caffeine to a concentration of from about 0 to about 100 g/l, and then adding to the resultant solution at least one diazonium salt to a concentration of from about 0.05 to about 15 mM of solution, to form a composition which has a pH of about 1.0 to about 6.0 and is stable at least 18 months at 2° C. to 8° C.

15. A method as claimed in claim 14 in which the at least one complexing agent is ethylenediaminetetraacetic acid present in a concentration of 2 g/l.

16. A method as claimed in claim 14 in which the at least one diazonium salt is 3,5 chlorophenol diazonium tetrafluoroborate.

17. A method as claimed in claim 16 in which the at least one water soluble organic sulfate is a lithium salt of dodecyl sulfate.

18. A method as claimed in claim 14 in which the at least one water soluble organic sulfate is selected from the group consisting of long chain aliphatic sulfates, aromatic sulfates and mixtures thereof.

19. A method as claimed in claim 14 in which the at least one diazonium salt is provided to a concentration of about 0.15 mM.

20. A composition as claimed in claim 19 in which the formed composition has a pH of about 3.5 to 5.5.

21. A method as claimed in claim 14 in which the formed composition has a pH of from about 3.5 to about 5.5.

* * * * *

UNITED STATES PATENT AND TRADEMARK OFFICE
CERTIFICATE OF CORRECTION

PATENT NO. : 4,965,210

DATED : October 23, 1990

INVENTOR(S) : Ivan E. Modrovich

It is certified that error appears in the above-identified patent and that said Letters Patent is hereby corrected as shown below:

Column 1, line 17, change "quantitive" to
-- quantitative --.

Column 2, line 53, change "hemaglobin" to
-- hemoglobin --.

Column 3, line 33, after "pH" and before "about"
delete -- is from --.

Signed and Sealed this

Fourteenth Day of July, 1992

Attest:

DOUGLAS B. COMER

*Attesting Officer*  *Acting Commissioner of Patents and Trademarks*